US00PP26252P2

(12) United States Plant Patent
van der Meer

(10) Patent No.: US PP26,252 P2
(45) Date of Patent: Dec. 22, 2015

(54) ***CHRYSANTHEMUM* PLANT NAMED 'BKGARDYL'**

(50) Latin Name: *Chrysanthemum×morifolium*
Varietal Denomination: Bkgardyl

(71) Applicant: Adrianus L. M. van der Meer, Monster (NL)

(72) Inventor: Adrianus L. M. van der Meer, Monster (NL)

(73) Assignee: Beekenkamp Plants B.V., Maasdijk (NL)

( * ) Notice: Subject to any disclaimer, the term of this patent is extended or adjusted under 35 U.S.C. 154(b) by 26 days.

(21) Appl. No.: 14/120,118

(22) Filed: Apr. 25, 2014

(51) Int. Cl.
*A01H 5/02* (2006.01)

(52) U.S. Cl.
USPC ..... Plt./289

(58) Field of Classification Search
USPC ..... Plt./289
CPC ..... A01H 5/0255; A01H 5/025; A01H 5/02; A01H 5/00
See application file for complete search history.

*Primary Examiner* — Kent L Bell
(74) *Attorney, Agent, or Firm* — C. A. Whealy

(57) ABSTRACT

A new and distinct cultivar of *Chrysanthemum* plant named 'Bkgardyl', characterized by its compact, upright and mounded plant habit; moderately vigorous growth habit; uniform flowering response; early and freely flowering habit; decorative-type inflorescences with bright yellow-colored ray florets; and good garden performance.

2 Drawing Sheets

Botanical designation: *Chrysanthemum×morifolium.*
Cultivar denomination: 'BKGARDYL'.

BACKGROUND OF THE INVENTION

The present invention relates to a new and distinct cultivar of *Chrysanthemum* plant, botanically known as *Chrysanthemum×morifolium*, commercially grown as a garden *Chrysanthemum* plant and hereinafter referred to by the name 'Bkgardyl'.

The new *Chrysanthemum* plant is a naturally-occurring whole plant mutation of the *Chrysanthemum×morifolium* 'Bkgardrs', not patented. The new *Chrysanthemum* plant was discovered by the Inventor in September, 2012 as a single flowering plant from within a population of plants of 'Bkgardrs' in a controlled greenhouse environment in Monster, The Netherlands.

Asexual reproduction of the new *Chrysanthemum* plant by vegetative tip cuttings was first conducted in Maasdijk, The Netherlands in December, 2012. Asexual reproduction by cuttings has shown that the unique features of this new *Chrysanthemum* plant are stable and reproduced true to type in successive generations.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Bkgardyl'. These characteristics in combination distinguish 'Bkgardyl' as a new and distinct garden *Chrysanthemum* plant:

1. Compact, upright and mounded plant habit.
2. Moderately vigorous growth habit.

3. Uniform flowering response.
4. Early and freely flowering habit.
5. Decorative-type inflorescences with bright yellow-colored ray florets.
6. Good garden performance.

Plants of the new *Chrysanthemum* differ from plants of the parent, 'Bkgardrs', primarily in ray floret coloration as plants of the new *Chrysanthemum* have bright yellow-colored ray florets whereas plants of 'Bkgardrs' have pink-colored ray florets.

Plants of the new *Chrysanthemum* can be compared to plants of *Chrysanthemum* 'Queenstown Yellow', not patented. In side-by-side comparisons conducted in Monster, The Netherlands, plants of the new *Chrysanthemum* differed from plants of 'Queenstown Yellow' in the following characteristics:

1. Plants of the new *Chrysanthemum* were denser and bushier than plants of 'Queenstown Yellow'.
2. Plants of the new *Chrysanthemum* had larger inflorescences than plants of 'Queenstown Yellow'.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type. Colors in the photographs may differ slightly from the color values cited in the detailed botanical description which accurately describe the colors of the new *Chrysanthemum* plant.

The photograph on the first sheet comprises a side perspective view of typical flowering plant of 'Bkgardyl' grown in a container.

The photograph on the second sheet is a close-up view of the upper (top of sheet) and lower (bottom of sheet) surfaces of typical inflorescences and leaves of 'Bkgardyl'.

DETAILED BOTANICAL DESCRIPTION

The aforementioned photographs and following observations and measurements describe plants grown in 12-cm containers during the winter in a glass-covered greenhouse in Maasdijk, The Netherlands and under cultural practices typical of commercial garden *Chrysanthemum* production. During the production of the plants, day and night temperatures ranged from about 18° C. to 19° C. and light levels averaged 7,000 lux. Plants were grown under photoinductive short day/long night treatments, pinched one time and were 68 days old when the photographs and description were taken. In the following description, color references are made to The Royal Horticultural Society Colour Chart, 2007 Edition, except where general terms of ordinary dictionary significance are used.

Botanical classification: *Chrysanthemum×morifolium* 'Bkgardyl'.

Parentage: Naturally-occurring whole plant mutation of the *Chrysanthemum×morifolium* 'Bkgardrs', not patented.

Propagation:

*Type*.—Terminal vegetative cuttings.

*Time to initiate roots, summer*.—About ten days at temperatures about 18° C. to 19° C.

*Time to initiate roots, winter*.—About twelve days at temperatures about 18° C. to 19° C.

*Time to produce a rooted young plant, summer*.—About 14 days at temperatures about 18° C. to 19° C.

*Time to produce a rooted young plant, winter*.—About 16 days at temperatures about 18° C. to 19° C.

*Root description*.—Medium in thickness, fibrous; white in color.

*Rooting habit*.—Freely branching; medium density.

Plant description:

*Plant and growth habit*.—Herbaceous garden type *Chrysanthemum* with decorative-type inflorescences; compact and bushy plant habit; plants roughly globular in shape, broadly upright and uniformly mounding; moderately vigorous growth habit; freely branching habit.

*Plant height*.—About 14.1 cm.

*Plant width*.—About 12.6 cm.

*Lateral branches*.—Length: About 9.1 cm. Diameter: About 2.5 mm. Internode length: About 8 mm. Strength: Strong. Texture: Densely pubescent. Color: Close to 144A.

Leaf description:

*Arrangement*.—Alternate, simple.

*Length*.—About 4.1 cm.

*Width*.—About 3.4 cm.

*Shape*.—Broadly ovate, palmately lobed.

*Apex*.—Acute.

*Base*.—Attenuate.

*Margin*.—Palmately lobed, sinuses between lateral lobes divergent to parallel; coarsely dentate.

*Texture, upper surface*.—Sparsely pubescent.

*Texture, lower surface*.—Densely pubescent; veins prominent.

*Color*.—Developing leaves, upper surface: Between 143A and 144A. Developing leaves, lower surface: Close to 143C. Fully expanded leaves, upper surface: Close to 137B; venation, close to 137B. Fully expanded leaves, lower surface: Close to 147B; venation, close to 144A.

*Petiole length*.—About 8 mm.

*Petiole diameter*.—About 2 mm.

*Petiole texture, upper and lower surfaces*.—Densely pubescent.

*Petiole color, upper surface*.—Close to 144A; towards the margins, close to 137B.

*Petiole color, lower surface*.—Close to 144A.

Inflorescence description:

*Appearance*.—Decorative-type inflorescence form with obovate-shaped ray florets; inflorescences borne on terminals above the foliar plane; disc and ray florets arranged acropetally on the capitulum.

*Fragrance*.—Faintly fragrant.

*Flowering response*.—Under natural season conditions, plants flower in the autumn in the Netherlands; under controlled greenhouse environment conditions, inflorescence initiation and development can be induced under short day/long night conditions (at least 13.5 hours of darkness); early flowering habit; plants flower about eight weeks after planting.

*Postproduction longevity*.—Inflorescences maintain good color and substance for about four weeks on the plant; inflorescences not persistent.

*Quantity of inflorescences*.—Freely flowering habit with about 21 inflorescences developing per plant.

*Inflorescence buds*.—Height: About 7 mm. Diameter: About 7 mm. Shape: Globular. Color: Close to 143A.

*Inflorescences*.—Diameter: About 3.2 cm. Depth (height): About 1.5 cm. Diameter of disc: About 1.1 cm. Receptacle diameter: About 2 mm. Receptacle height: About 2 mm. Receptacle color: Close to 144C.

*Ray florets*.—Orientation: Initially upright, then about 20° from perpendicular to peduncle. Number of ray florets per inflorescence: About 50 arranged in about four whorls. Length: About 1.1 cm. Width: About 4.5 mm. Shape: Obovate. Apex: Obtuse. Base: Cuneate. Margin: Entire. Texture, upper and lower surfaces: Smooth, glabrous, velvety; longitudinally ridged. Color: When opening and fully opened, upper surface: Close to 5B; color does not fade with development. When opening and fully opened, lower surface: Close to 6D; color does not fade with development.

*Disc florets*.—Arrangement: Massed at center of receptacle. Number of disc florets per inflorescence: About 50. Shape: Deformed; similar to ray florets in shape, roughly obovate. Apex: Obtuse. Base: Cuneate. Margin: Entire, strongly involute. Length: About 7.5 mm. Width: About 1 mm. Texture, upper and lower surfaces: Smooth, glabrous. Color: When opening and fully opened, upper surface: Close to 5B. When opening and fully opened, lower surface: Close to 6D.

*Phyllaries*.—Number of phyllaries per inflorescence: About 24 arranged in about three whorls. Length: About 6 mm. Width: About 2.5 mm. Shape: Ovate. Apex: Bluntly acute. Base: Cuneate. Texture, upper surface: Smooth, glabrous. Texture, lower surface: Sparsely pubescent. Color, upper and lower surfaces: Close to 137B to 137C; margins, close to 148D.

*Peduncles*.—Length: First peduncle: About 2.1 cm. Fourth peduncle: About 2.7 cm. Diameter (first peduncle): About 1.5 mm. Angle: Terminal peduncle, erect; secondary peduncles, about 45° from vertical. Strength: Strong, flexible. Texture: Densely pubescent. Color: Close to 147B.

*Reproductive organs*.—Androecium: None observed. Gynoecium: None observed.

*Seeds and fruits*.—Seed and fruit production has not been observed on plants of the new *Chrysanthemum*.

Disease & pest resistance: Resistance to pathogens and pests common to *Chrysanthemum* plants has not been observed on plants of the new *Chrysanthemum* grown under commercial conditions.

Garden performance: Plants of the new *Chrysanthemum* have been observed to have good garden performance, to tolerate high temperatures of about 35° C. and to be hardy to USDA Hardiness Zones 7 to 8.

It is claimed:

1. A new and distinct *Chrysanthemum* plant named 'Bkgardyl' as illustrated and described.

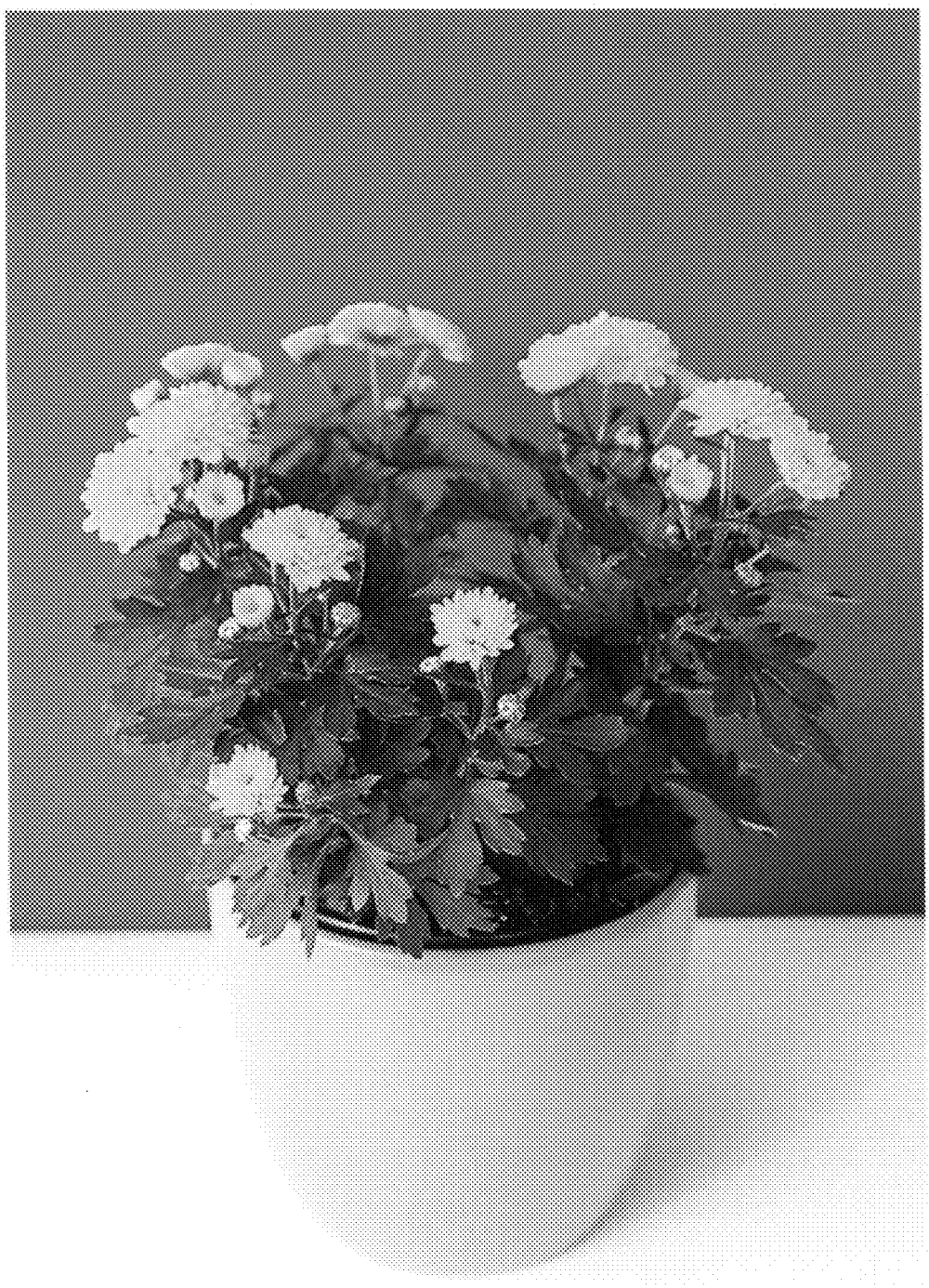

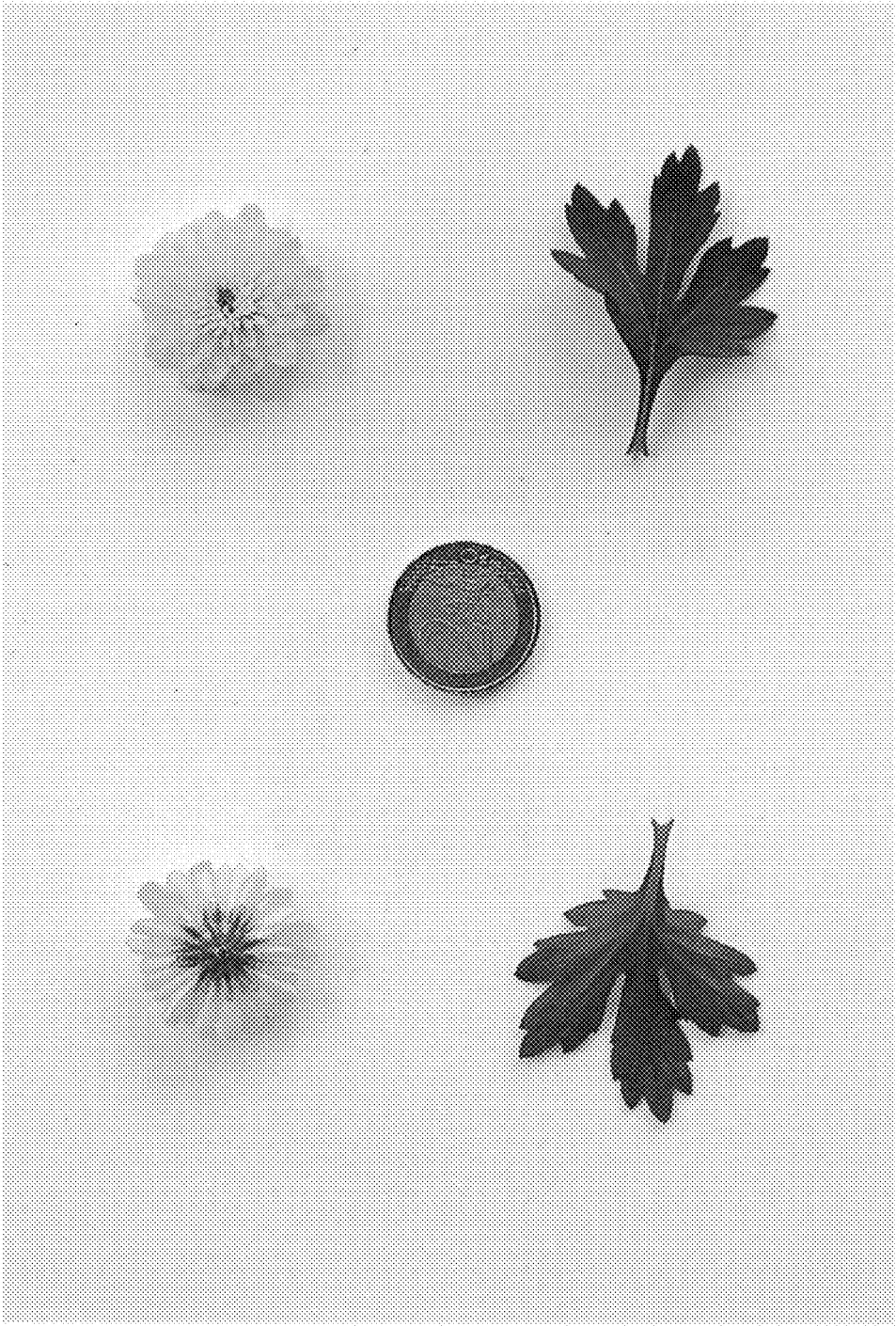

* * * * *